(12) United States Patent
Lee et al.

(10) Patent No.: US 8,729,169 B2
(45) Date of Patent: May 20, 2014

(54) SYNTHETIC RUBBER WITH ANTI-OXIDANTS FOR RUBBER

(75) Inventors: Hyung Jae Lee, Daejeon (KR); Chang Kyo Shin, Daejeon (KR); Jin Eok Kim, Daejeon (KR)

(73) Assignee: Korea Kumho Petrochemical Co., Ltd., Seoul (KR)

( * ) Notice: Subject to any disclaimer, the term of this patent is extended or adjusted under 35 U.S.C. 154(b) by 109 days.

(21) Appl. No.: 13/498,533

(22) PCT Filed: Apr. 8, 2011

(86) PCT No.: PCT/KR2011/002469
§ 371 (c)(1), (2), (4) Date: Mar. 27, 2012

(87) PCT Pub. No.: WO2012/138001
PCT Pub. Date: Oct. 11, 2012

(65) Prior Publication Data
US 2012/0270982 A1    Oct. 25, 2012

(51) Int. Cl.
*C08K 5/36* (2006.01)
*C08L 9/06* (2006.01)

(52) U.S. Cl.
USPC ............................................. 524/325; 568/47

(58) Field of Classification Search
USPC ............................................. 524/325; 568/47
See application file for complete search history.

(56) References Cited

U.S. PATENT DOCUMENTS

2001/0044518 A1    11/2001    Hoffmann et al.

FOREIGN PATENT DOCUMENTS

| KR | 10-0172941 | 3/1999 | |
| KR | 10-2011-0027402 | 3/2011 | |
| KR | 1020110027402 A | * 3/2011 | ............ C07C 321/20 |

OTHER PUBLICATIONS

International Search Report mailed Jan. 10, 2012 for PCT/KR2011/002469.
Written Opinion of ISA mailed Jan. 10, 2012 for PCT/KR2011/002469.

* cited by examiner

*Primary Examiner* — Robert D. Harlan
(74) *Attorney, Agent, or Firm* — Lowe Hauptman & Ham, LLP.

(57) ABSTRACT

Disclosed are a novel anti-oxidant for rubber and a synthetic rubber including the same. The disclosed anti-oxidant contains a thio compound. The rubber including the anti-oxidant has excellent thermostability at a temperature of 100° C. or higher, and the anti-oxidant shows a low volatility due to its high molecular weight thus being applicable to manufacture environment-friendly rubber.

4 Claims, No Drawings

SYNTHETIC RUBBER WITH ANTI-OXIDANTS FOR RUBBER

CROSS-REFERENCE TO RELATED APPLICATION

This application claims the benefit of International Patent Application No. PCT/KR2011/002469 filed on Apr. 8, 2011, the entire contents of which are incorporated herein by reference.

BACKGROUND (a) Technical Field

The present invention relates to an anti-oxidant for rubber and synthetic rubber including the same, wherein the anti-oxidant contains a highly heat-resistant and environment-friendly thio compound.

(b) Background Art

In general, the conventional anti-oxidants of polymers can be classified into phenol-based, amine-based, phosphite-based, and thioester-based anti-oxidants. These anti-oxidants may be used alone or in any combination thereof. However, each of the anti-oxidants has its own limitation. Specifically, the phenol-based anti-oxidant shows a high thermostability at the initial stage, but is frequently colored after oxidation. Thus, its use has been largely limited. The amine-based anti-oxidant is excellent as an anti-oxidant, but has a problem in its color. The phosphite-based anti-oxidant has a disadvantage that it is hydrolyzed by water, and is decomposed in a stripping process during rubber synthesis. The thioester-based anti-oxidant normally cannot exhibit its performance when used alone but can only when used in combination with a primary anti-oxidant.

2,6-di-t-butyl-4-methylphenol (hereinafter, referred to as "BHT") generally used in a polymer is a primary anti-oxidant, and is excellent in thermostability. However, it is volatile due to low molecular weight thus lowering its function as a heat-resistant additive while causing serious discoloration. Especially, the BHT may damage the liver, and cause allergies and tumors.

Since the BHT generally used in polymers can cause environmental pollution due to its volatility, BHT-free products have been required in industry. Accordingly, there is an urgent need for the development of an anti-oxidant that can prevent oxidation of polymers and maintain the intrinsic properties of the polymers, while not being harmful to human body and having low volatility.

At present, as BHT replacement materials, 1076(octadecyl-3-(3,5-di-t-butyl-4-hyroxyphenyl)-propionate), 1010 (pentaerythrityl-tetrakis[3-(3,5-di-t-butyl-4-hyroxyphenyl)-propionate]), etc., are used. However, they are merely primary anti-oxidants, and have limitations in their performance and physical properties thus requiring addition of a secondary anti-oxidant.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

Accordingly, in order to improve problems of the conventional anti-oxidant, the inventors of the present invention used a thio compound represented by Formula 1 as a rubber additive. As a result, they found that the compound has both functions of a primary anti-oxidant and a secondary anti-oxidant in one molecule, and thus can be used alone without combining with a primary anti-oxidant or a secondary anti-oxidant. Further, they found that it is possible to maintain the thermostability of rubber by using the compound in an amount smaller than that of a conventional anti-oxidant, thereby completing this invention.

[Formula 1]

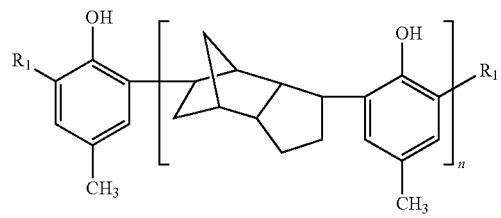

In Formula 1, $R_1$ represents $-CH_2SR_2$, $R_2$ represents a linear, branched or cyclic C5-C16 alkyl group or a C6-C16 aromatic compound, and n represents a real number ($1 \leq n \leq 20$).

Accordingly, an object of the present invention is to provide an anti-oxidant for rubber, and a synthetic rubber including the same, the anti-oxidant containing a thio compound.

In one aspect, the present invention provides an anti-oxidant for rubber, including a thio compound represented by Formula 1 below:

[Formula 1]

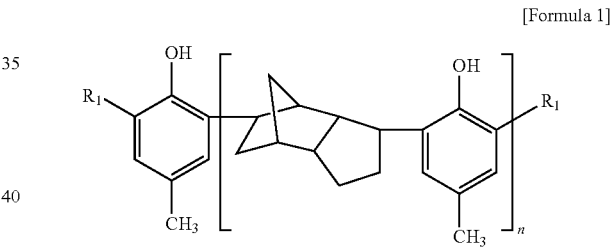

wherein in Formula 1, $R_1$ represents $-CH_2SR_2$, $R_2$ represents a linear, branched or cyclic C5-C16 alkyl group or a C6-C16 aromatic compound, and n represents a real number ($1 \leq n \leq 20$).

In another aspect, the present invention provides synthetic rubber including the anti-oxidant for the rubber.

The anti-oxidant for rubber of the present invention when used alone can show an effect of both primary and secondary anti-oxidants. Also, although it is used in a small amount, it is possible to maintain the thermostability of rubber. Furthermore, it has a lower volatility than that of conventional anti-oxidants, and is thus very environment-friendly.

Other aspects and exemplary embodiments of the invention are discussed infra.

The above and other features of the invention are discussed infra.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

The present invention relates to a novel anti-oxidant for rubber, and a synthetic rubber including the same, the anti-oxidant containing a thio compound represented by Formula 1.

[Formula 1]

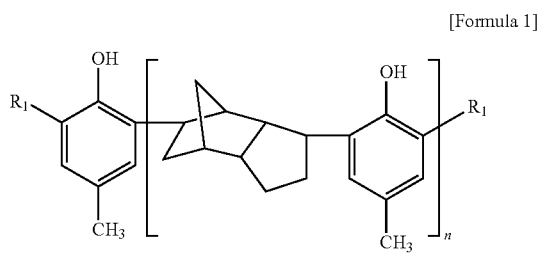

In Formula 1, $R_1$ represents —$CH_2SR_2$, $R_2$ represents a linear, branched or cyclic C5-C16 alkyl group or a C6-C16 aromatic compound, and n represents a real number ($1 \leq n \leq 20$).

The anti-oxidant includes the thio compound represented by Formula 1. In Formula 1, preferably, $R_1$ may be a C6-C14 thio compound, and more preferably, $R_2$ may be one kind or a mixture of two or more kinds selected from the group consisting of thio compounds having 8, 10 and 12 carbon atoms.

The anti-oxidant for rubber may be used in an amount of 0.01 to 5 parts by weight, preferably 0.05 to 3 parts by weight, and more preferably 0.1 to 2 parts by weight, relative to 100 parts by weight of synthetic rubber including at least one selected from the group consisting of a butadiene polymer, a styrene-butadiene copolymer, a random styrene-butadiene copolymer, a styrene-butadiene-styrene block copolymer, a styrene-butadiene block copolymer and multi-block copolymers of styrene-butadiene-styrene-butadiene. Here, when the anti-oxidant for rubber is used less than 0.01 parts by weight relative to 100 parts by weight of the synthetic rubber, the thermostability due to lack of anti-oxidant cannot be achieved. On the other hand, when it is used more than 5 parts by weight, it becomes not economical. Thus, it is preferred that the anti-oxidant be used within the above mentioned range.

The rubber including the anti-oxidant has excellent thermostability at a temperature of 100° C. or higher, and the anti-oxidant shows a low volatility due to its high molecular weight. Thus, it is possible to prepare environment-friendly rubber.

EXAMPLES

The following examples illustrate the present invention and are not intended to limit the same.

Synthesis of Thio Compound

Synthesis Example 1

Preparation of Alkylation Compound p-cresol (324 g) was mixed with BF$_3$ ether solution (boron trifluoride etherate) (5.5 g), and heated up to 90. Dicyclopentadiene (132 g) was slowly added thereto for 1 hour. After a 3 hour reaction, the resulting solution was concentrated at 190° C. and 15 mmHg to obtain 300 g of an alkylation compound.

Preparation Example 1

Preparation of a Thio Compound Represented by Formula 1-1 Below

The alkylation compound (1 equivalent) prepared in Synthesis Example 1 was dissolved in an equal amount of toluene. Paraformaldehyde (2 equivalents), octylmercaptan (2 equivalents), and 50% dimethylamine (0.2 equivalents) aqueous solution were added thereto, followed by a reaction at 100° C. for 3 hours. Then, an organic layer separated from the reaction solution was concentrated under vacuum to obtain a concentrated pale brown solid, i.e., a thio compound (Formula 1-1). The result is shown in Table 1 below.

[Formula 1-1]

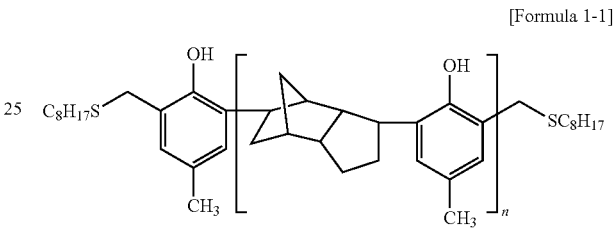

(n = 1~6)

Preparation Example 2

Preparation of a Thio Compound Represented by Formula 1-2 Below

A thio compound (Formula 1-2) was prepared the same as in Preparation Example 1 except that decanylmercaptan was used instead of octylmercaptan. The result is shown in Table 1 below.

[Formula 1-2]

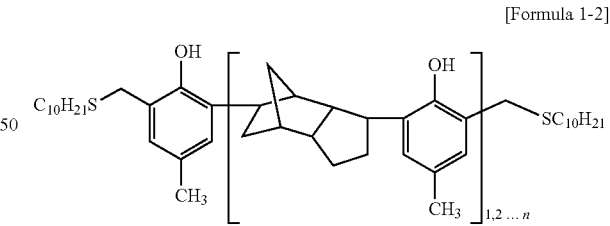

(n = 1~6)

Preparation Example 3

Preparation of a Thio Compound Represented by Formula 1-3 Below

A thio compound (Formula 1-3) was prepared the same as in Preparation Example 1 except that dodecanylmercaptan was used instead of octylmercaptan. The result is shown in Table 1 below.

[Formula 1-3]

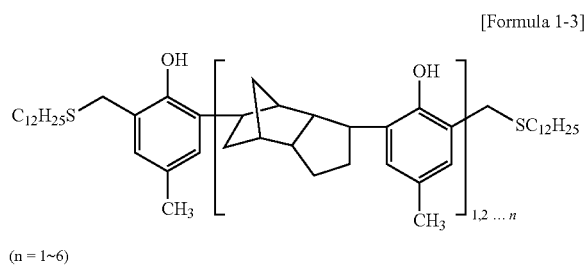

(n = 1~6)

TABLE 1

| index | mercaptan | reaction condition | conversion (%) | purity (%) |
|---|---|---|---|---|
| Preparation Example 1 | octylmercaptan | 100° C., 3 hours | 99 | 95 |
| Preparation Example 2 | decanylmercaptan | 100° C., 3 hours | 97 | 93 |
| Preparation Example 3 | dodecanylmercaptan | 120° C., 2 hours | 95 | 92 |

Preparation of Synthetic Rubber

Example 1

100 parts by weight of Butadiene rubber (commercial name: Kumho KBR 01, raw Mooney viscosity: 45, cis content: 94% or more) prepared by a conventional method was added with the thio compound prepared in Preparation Example 1 to obtain synthetic rubber.

Example 2

Synthetic rubber having the composition as noted in Table 2 below was prepared the same as in Example 1, except that styrene-butadiene rubber (commercial name: Kumho 1502, raw Mooney viscosity 52, styrene content 23.5%) was used instead of butadiene rubber

Example 3

Synthetic rubber was prepared the same as in Example 1, except that the thio compound prepared in Preparation Example 2 was used instead of the thio compound prepared in Preparation Example 1.

Example 4

Synthetic rubber was prepared the same as in Example 2, except that the thio compound prepared in Preparation Example 2 was used instead of the thio compound prepared in Preparation Example 1.

Example 5

Synthetic rubber was prepared the same as in Example 1, except that the thio compound prepared in Preparation Example 3 was used instead of the thio compound prepared in Preparation Example 1.

Example 6

Synthetic rubber was prepared the same as in Example 2, except that the thio compound prepared in Preparation Example 3 was used instead of the thio compound prepared in Preparation Example 1.

Comparative Examples 1~4

Synthetic rubber was prepared the same as in Example 1 in such a manner that the synthetic rubber can have the compositions shown in Table 1 below.

TABLE 2

| index | butadiene rubber | styrene-butadiene rubber | Anti-oxidant (parts by weight) | | | | |
|---|---|---|---|---|---|---|---|
| | | | Preparation Example 1 | Preparation Example 2 | Preparation Example 3 | BHT[1] | AO 1076[2] |
| Ex. 1 | 100 | — | 0.2 | — | — | — | — |
| Ex. 2 | — | 100 | 0.2 | — | — | — | — |
| Ex. 3 | 100 | — | — | 0.2 | — | — | — |
| Ex. 4 | — | 100 | — | 0.2 | — | — | — |
| Ex. 5 | 100 | — | — | — | 0.2 | — | — |
| Ex. 6 | — | 100 | — | — | 0.2 | — | — |
| Comp. Ex. 1 | 100 | — | — | — | — | 0.4 | — |
| Comp. Ex. 2 | — | 100 | — | — | — | 0.4 | — |
| Comp. Ex. 3 | 100 | — | — | — | — | — | 0.4 |
| Comp. Ex. 4 | — | 100 | — | — | — | — | 0.4 |

[1]BHT: 2,6-di-t-butyl-4-methylphenol(Aldrich)
[2]AO 1076: octadecyl-3-(3,5-di-t-butyl-4-hyroxyphenyl)-propionate (Ciba Company, commercial name Irganox 1076)

Test Examples

Test Example 1

Thermostability Test (Gel Rank Test)

Synthetic rubbers obtained from Examples 1~6 and Comparative Examples 1~4 were steam-stripped to obtain rubber crumbs. The rubber crumbs were dried by roll milling at 110° C. to obtain test pieces for thermal aging test. The test pieces were thermally aged at 120° C. for 60, 90, 120 and 150 minutes, and then dissolved in toluene and filtered. Then, the test pieces were dyed with a solution of Solvent Blue35, and the state of formed gels (the size and the number of gels) were examined by naked eye (see Table 3 below, A: a smaller size and smaller number of gels, D: a larger size and larger number of gels) to measure the thermostability. The result is shown in Table 3 below.

TABLE 3

| index | 60 min | 90 min | 120 min | 150 min |
|---|---|---|---|---|
| Example 1 | A | A | A | A |
| Example 2 | A | A | A | A |
| Example 3 | A | A | A | A |
| Example 4 | A | A | A | A |
| Example 5 | A | A | A | B |
| Example 6 | A | A | A | B |
| Comparative Example 1 | A | A | C | D |
| Comparative Example 2 | A | A | C | D |
| Comparative Example 3 | A | A | A | B |
| Comparative Example 4 | A | A | A | B |

A: very good, B: good, C: normal, D: bad

Test Example 2

Thermostability Test (Mooney Viscosity Test)

Synthetic rubbers obtained from Examples 1~6 and Comparative Examples 1~4 were steam-stripped so as to obtain rubber crumbs. Then, the rubber crumbs were dried by roll milling at 110° C. to obtain test samples for thermal aging test. The test samples were thermally aged at 130° C. for 60 minutes, and then their Mooney viscosity was measured by using Mooney MV 2000 (ALPHA Technology) at 100° C. The result is shown in Table 4 below. $ML_{1+4}$, 100° C. in Table 4 below indicates that the measurement was carried out for 4 minutes at 100° C. after pre-heating for 1 minute.

TABLE 4

| index | Anti-oxidant content (parts by weight) | Mooney viscosity at 0 hour ($ML_{1+4}$, 100° C.) | Mooney viscosity after 4 hours ($ML_{1+4}$, 100° C.) | ΔMV |
|---|---|---|---|---|
| Example 1 | 0.2 | 37.7 | 33.3 | 4.4 |
| Example 2 | 0.2 | 37.4 | 33.6 | 3.8 |
| Example 3 | 0.2 | 37.5 | 33.2 | 4.3 |
| Example 4 | 0.2 | 37.7 | 32.1 | 5.6 |
| Example 5 | 0.2 | 37.6 | 31.3 | 6.3 |
| Example 6 | 0.2 | 37.6 | 30.7 | 6.9 |
| Comparative Example 1 | 0.4 | 37.8 | 26.6 | 11.2 |
| Comparative Example 2 | 0.4 | 37.3 | 27.0 | 10.8 |
| Comparative Example 3 | 0.4 | 37.6 | 25.8 | 11.8 |
| Comparative Example 4 | 0.4 | 37.6 | 26.2 | 11.4 |

In Table 4, the test samples from Examples 1~6 showed a smaller difference in Mooney viscosity (MV) than those in Comparative Examples, although in the test samples from Example 1~6, the amount of anti-oxidant used was half the amount used in Comparative Examples 1~4. Thus, it was found that the viscosity of rubber can be maintained. Also, from this result, it was confirmed that the thio compound of the present invention shows an anti-oxidative effect at least 2 fold higher than those of conventional anti-oxidants.

As described above, the thio compound of the present invention solves the existing problem in volatility by increasing its molecular weight using dicyclopentadiene. Further, it was confirmed that the thio compound of the present invention is an antioxidant with a dual function of a primary anti-oxidant and a secondary anti-oxidant. Still further, the thio compound of the present invention has superior thermostability to the conventional anti-oxidants such as BHT and AO 1076, even with a lesser amount.

The anti-oxidant for rubber of the present invention is suitable for use in synthetic rubber. Also, due to the excellent heat-resistance and physical properties, the synthetic rubber can be applicable to a plastic modifier, especially an impact-resistant polymerstyrene resin, a polymerstyrene sheet, a tire, and a hot-melt adhesive.

The invention has been described in detail with reference to exemplary embodiments thereof. However, it will be appreciated by those skilled in the art that changes may be made in these embodiments without departing from the principles and spirit of the invention, the scope of which is defined in the appended claims and their equivalents.

What is claimed is:

1. Synthetic rubber comprising an anti-oxidant for rubber, wherein the anti-oxidant for the rubber is in an amount of 0.01~5 parts by weight relative to 100 parts by weight of rubber and comprises a thio compound represented by Formula 1 below:

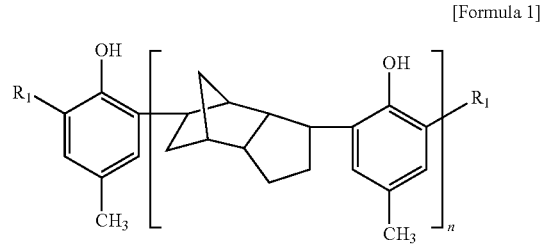

[Formula 1]

wherein in Formula 1, $R_1$ represents —$CH_2SR_2$, $R_2$ represents a linear, branched or cyclic C5-C16 alkyl group or a C6-C16 aromatic compound, and n represents a real number (1≤n≤20).

2. The synthetic rubber according to claim 1, wherein in Formula 1, $R_2$ comprises at least one selected from the group consisting of thio compounds with 8, 10 and 12 carbon atoms.

3. The synthetic rubber according to claim 1, wherein the rubber comprises at least one selected from the group consisting of a butadiene polymer, a styrene-butadiene copolymer, a random styrene-butadiene copolymer, a styrene-butadiene-styrene block copolymer, a styrene-butadiene block copolymer and multi-block copolymers of styrene-butadiene-styrene-butadiene.

4. The synthetic rubber according to claim 2, wherein the rubber comprises at least one selected from the group consisting of a butadiene polymer, a styrene-butadiene copolymer, a random styrene-butadiene copolymer, a styrene-butadiene-styrene block copolymer, a styrene-butadiene block copolymer and multi-block copolymers of styrene-butadiene-styrene-butadiene.

* * * * *